United States Patent [19]

Stella

[11] Patent Number: 6,133,248
[45] Date of Patent: Oct. 17, 2000

[54] POLAR DRUG OF PRODRUG COMPOSITIONS WITH EXTENDED SHELF-LIFE STORAGE AND A METHOD OF MAKING THEREOF

[75] Inventor: Valentino J. Stella, Lawrence, Kans.

[73] Assignee: Cydex, Inc., Overland Park, Kans.

[21] Appl. No.: 09/096,747

[22] Filed: Jun. 12, 1998

Related U.S. Application Data

[60] Provisional application No. 60/050,909, Jun. 13, 1997.

[51] Int. Cl.[7] .................. A61K 31/715; A61K 31/56; A61K 31/415
[52] U.S. Cl. ................. 514/58; 514/169; 514/385; 536/103
[58] Field of Search ................. 514/58, 169, 170, 514/171, 385; 536/103

[56] References Cited

U.S. PATENT DOCUMENTS

| | | | |
|---|---|---|---|
| 4,535,152 | 8/1985 | Szejtli et al. | 536/103 |
| 4,925,860 | 5/1990 | Hebranson et al. | 514/359 |
| 5,134,127 | 7/1992 | Stella et al. | 514/58 |
| 5,324,718 | 6/1994 | Loftsson | 514/58 |
| 5,376,645 | 12/1994 | Stella et al. | 514/58 |

FOREIGN PATENT DOCUMENTS

| | | |
|---|---|---|
| 0 163 433 A2 | 12/1985 | European Pat. Off. . |
| 0 188 821 A2 | 7/1986 | European Pat. Off. . |
| 0 213 514 A2 | 3/1987 | European Pat. Off. . |
| 0 839 528 A1 | 5/1998 | European Pat. Off. . |
| 39 38 227 C1 | 5/1991 | Germany . |
| WO 94/02518 | 2/1994 | WIPO . |

OTHER PUBLICATIONS

Rajewski et al. "Preliminary Safety Evaluation f Parenterally Administered Sulfoalkyl Ether beta–Cyclodextrin Derivatives", Journal of Pharmaceutical Sciences, vol. 84(8): 927–932, Aug. 1995.

Kazuto Okimoto et al. "The Interaction of Charged and Uncharged Drugs with Neutral (HP–B–CD) and Anionically Charged (SBE7–B–CD) B–Cyclodextrins", Pharmaceutical Research, vol. 13, No. 2 (1996) pp. 256–264.

Thorsteinn Loftsson et al. "Pharmaceutical Applications of Cyclodextrins. 1. Drug Solubilization and Stabilization", Journal of Pharmaceutical Sciences, vol..85, No. 10 (Oct. 1996) pp. 1017–1025.

S.A. Varia et al. "Phenytoin Prodrugs IV: Hydrolysis of Various 3–(Hydroxymethyl) phenytoin Esters", Journal of Pharmaceutical Sciences, vol. 73, No. 8 (Aug. 1984) pp. 1074–1080.

Loftsson et al., "Effects of cyclodextrins on the chemical stability of drugs in aqueous solutions", Drug Stability, vol. 1, No. 1 (1995) pp. 22–33.

Menard et al., "Studies of the Effect of pH, Temperature and Ring Size on the Complexation of Phenytoin with Cyclodextrins", Pharmaceutica Acta Helvetiae, vol. 63, No. 11 (1988) pp. 303–308.

Stella, "A case for prodrugs: Fosphenytoin", Advanced Drug Delivery Reviews, vol. 19, No. 2. (1996) pp. 311–330.

Muller et al., "Determination of the position of the ester bond in a micellar prodrug of phenytoin", International Journal of Pharmaceutics, vol. 102 (1994) pp. 109–116.

*Primary Examiner*—Howard C. Lee
*Attorney, Agent, or Firm*—Birch, Stewart, Kolasch & Birch, LLP

[57] ABSTRACT

The present invention is drawn to pharmaceutical composition comprising cyclodextrin and a pharmaceutically active agent or prodrug, wherein the cyclodextrin is present at less than 75% equimolar amounts of the above agent or prodrug. The present invention is further drawn to a method of extending the shelf-life of a pharmaceutically active agent or prodrug by adding one or more cyclodextrins a less than 75% equimolar amounts to said pharmaceutically active agent or prodrug.

27 Claims, 7 Drawing Sheets

*Production of Phenytoin from Degradation of Fosphenytoin at 25°C in 0.02 M Tris Buffer Solution*

(pH 7.4)

(pH 8.0)

POLAR DRUG OF PRODRUG COMPOSITIONS WITH EXTENDED SHELF-LIFE STORAGE AND A METHOD OF MAKING THEREOF

This application claims benefit of Provisional Appl. 60/050,909 filed Jun. 13, 1997.

FIELD OF THE INVENTION

The present invention is drawn to polar drug or prodrug compositions having an extended shelf-life. The present invention further encompasses a method of extending the shelf-life of polar drugs or prodrugs which have degradants which are poorly water soluble.

BACKGROUND OF THE INVENTION

Many polar drugs and prodrugs have a limited shelf-life not due to a loss in potency in the compounds them selves but due to the nucleation/precipitation of their degradants which are poorly water soluble. The impact of the poorly water soluble degradants on the shelf-life of drugs and prodrugs can be demonstrated by the following example. A drug formulated at 10 mg/ml which has a degradant with a solubility of 10 μg/ml (in parent drug molar equivalents) can only tolerate a 0.1% degradation before the degradant may precipitate from solution and render the drug unusable.

Since the presence of particulate species is undesirable, particularly with injectable drugs and prodrugs, the parent drug or prodrug must have very good chemical stability to provide a desired two-year shelf-life. Because of a lack of stability, it is not possible to obtain a long, minimum of two years, shelf-life with many of the water soluble prodrugs of insoluble drugs or with water soluble drugs which have insoluble degradants. The shelf-life of water-soluble prodrugs or drugs is further complicated and shortened if there is any degradant present in the original product as a contaminant.

One example of a water soluble prodrug of a water insoluble drug is fosphenytoin. Fosphenytoin has been developed as a water soluble prodrug of the active drug compound phenytoin (U.S. Pat. No. 4,925,860; Varia et al., J. Pharm. Sci. 73, 1074–1080, 1984). When fosphenytoin is formulated as fosphenytoin dihydrate at a concentration of 80.6 mg/ml or as anhydrous fosphenytoin at a concentration of 75 mg/ml, it decomposes at pH values less than 8.0 primarily to phenytoin, which has an intrinsic aqueous solubility of less than 25 μg/ml. Because of the poor aqueous solubility of phenytoin, at pH values of either 7.4 or 8.0 in 0.02 M Tris buffer, only about 0.1% degradation of fosphenytoin can be tolerated before nucleation of phenytoin occurs.

To overcome the solubility problems of phenytoin, the prodrug fosphenytoin is generally formulated at a high pH of 8.5 (U.S. Pat. No. 4,925,860). However, fosphenytoin is actually more stable at a lower pH. Because of the instability of fosphenytoin at high pH values, it is only possible to obtain a shelf-life of two years for the prodrug product by refrigeration. In addition, the high pH needed is less physiologically acceptable and the degradants are more complex in structure, raising the issue of toxicity from degradants.

Numerous prior art references, including Okimoto et al., Pharm. Res. 13:256–264; Loftsson and Brewster, J. Pharm. Sci. 85:1017–1025; and U.S. Pat. No. 5,134,127, teach compositions of cyclodextrins with drugs. These compositions of the prior art teach at least equimolar amounts of cyclodextrin and drug for the purpose of solubilizing the drug. To our knowledge, the issue of solubilization of poorly soluble degradants in the presence of high concentrations of parent drug has not been addressed either in the scientific or patent literature.

SUMMARY OF THE INVENTION

One object of the present invention is to provide pharmaceutical compositions of polar drugs or prodrugs having an extended shelf-life comprising cyclodextrin, a pharmaceutically active agent or prodrug and a pharmaceutically acceptable carrier, wherein the cyclodextrin is present as less than 75% equimolar amounts of the active agent but does not exclude high molar equivalents from being used.

Another object of the present invention is to provide pharmaceutical compositions of polar drugs or prodrugs having a suitable pH and comprising cyclodextrin and a pharmaceutically active agent or prodrug, wherein the shelf-life of the pharmaceutical composition is at least two years when stored at room temperature.

The present invention is further drawn to a method of extending the half-life of polar drugs and prodrugs comprising adding one or more cyclodextrins at less than 75%, more preferably less than 50%, total equimolar amount to a composition containing a pharmaceutically active agent or prodrug.

DETAILED DESCRIPTION OF THE INVENTION

Figure 1:
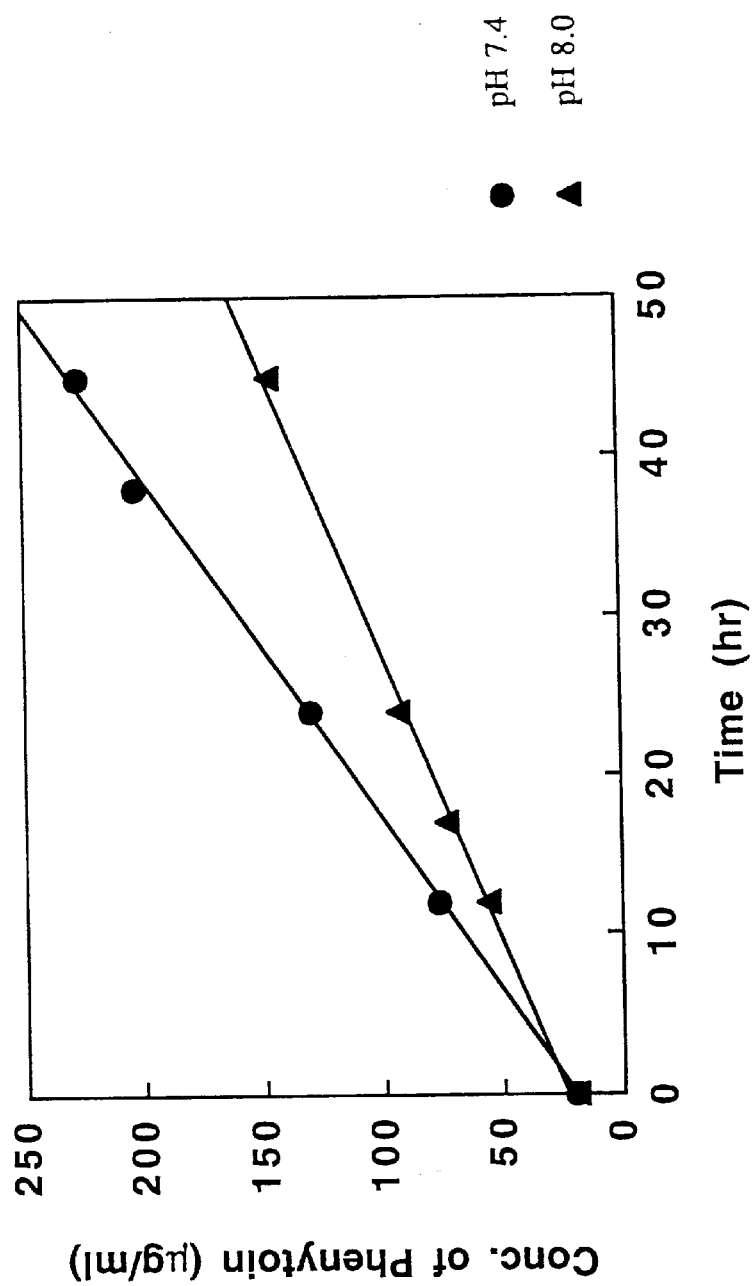
FIG. 1 shows the production of phenytoin from the degradation of fosphenytoin at 60° C. in 0.02M Tris buffer solution. Circles present phenytoin production at pH 7.4. Triangles present phenytoin production at pH 8.0.
Figure 2A:
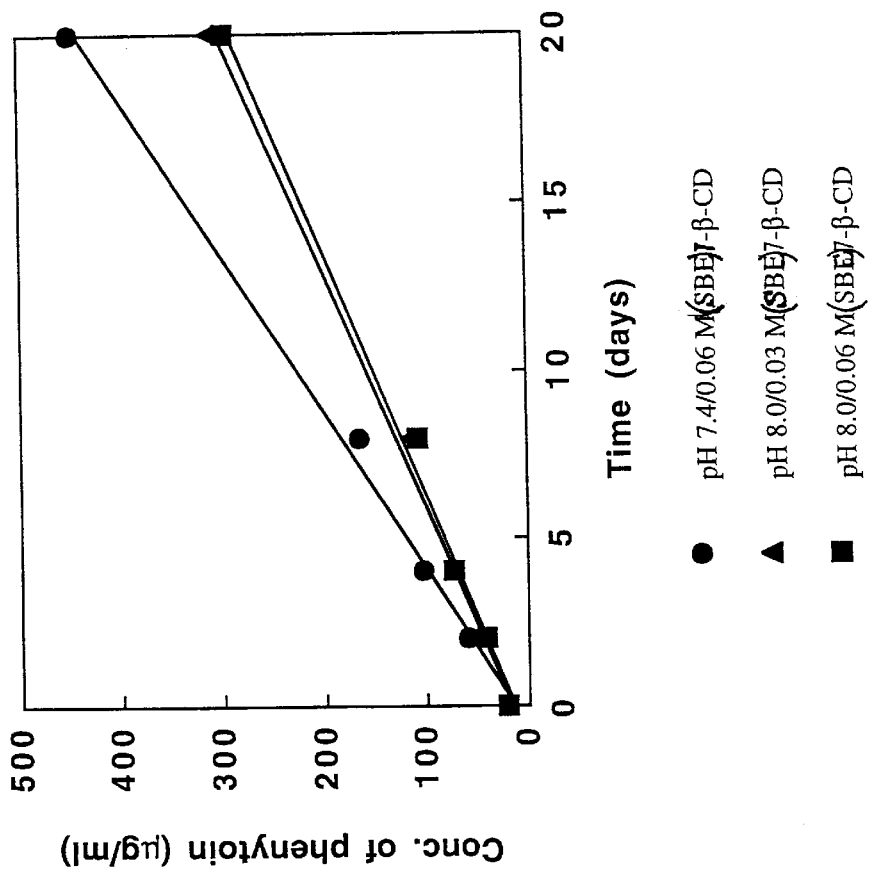
FIG. 2A shows the effects of cyclodextrin (SBE)7m-β-CD on the production of phenytoin from the degradation of fosphenytoin at 50° C. and with pH 7.4/0.06M (SBE)7m-β-CD (—●—); pH 8.0/0.03M (SBE)7m-β-CD (—▲—); and pH 8.0/0.06M (SBE)7m-β-CD (—■—).
Figure 2B:
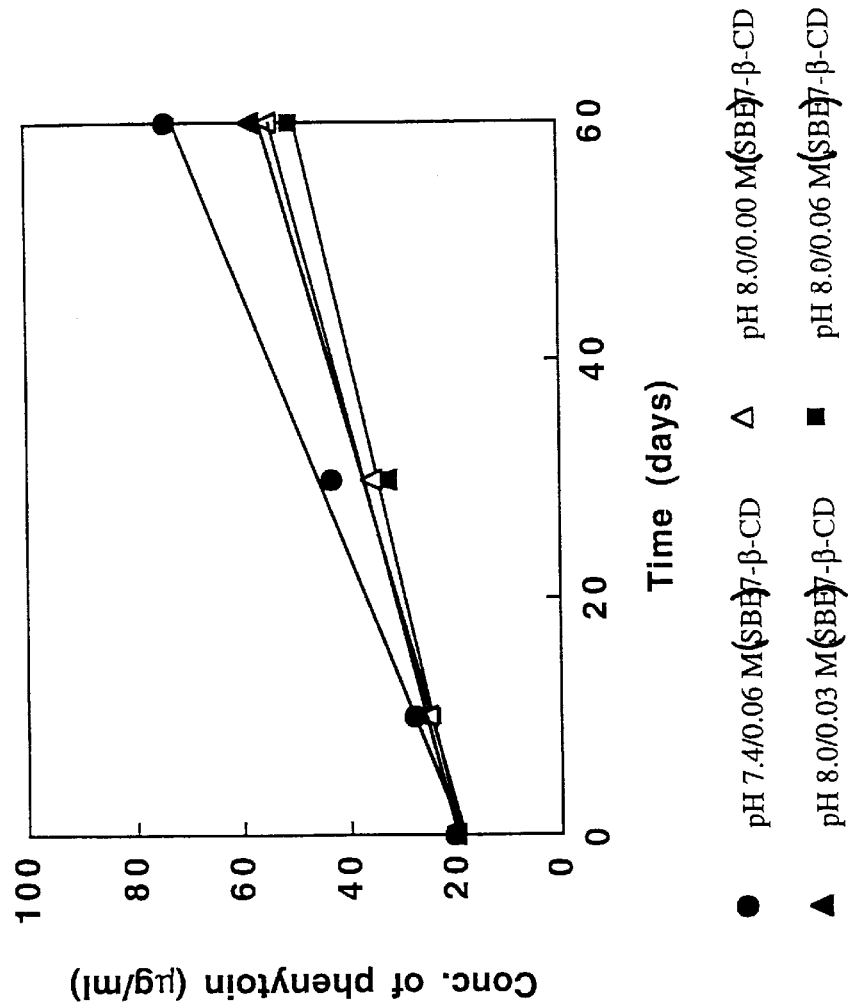
FIG. 2B shows the effects of cyclodextrin (SBE)7m-β-CD on the production of phenytoin from the degradation of fosphenytoin at 37° C. and with pH 7.4/0.06M (SBE)7m-β-CD (—●—); pH 8.0/0.03M (SBE)7m-β-CD (—▲—); pH 8.0/0.00M (SBE)7m-β-CD (—Δ—); and pH 8.0/0.06M (SBE)7M-β-CD (—■—).
Figure 2C:
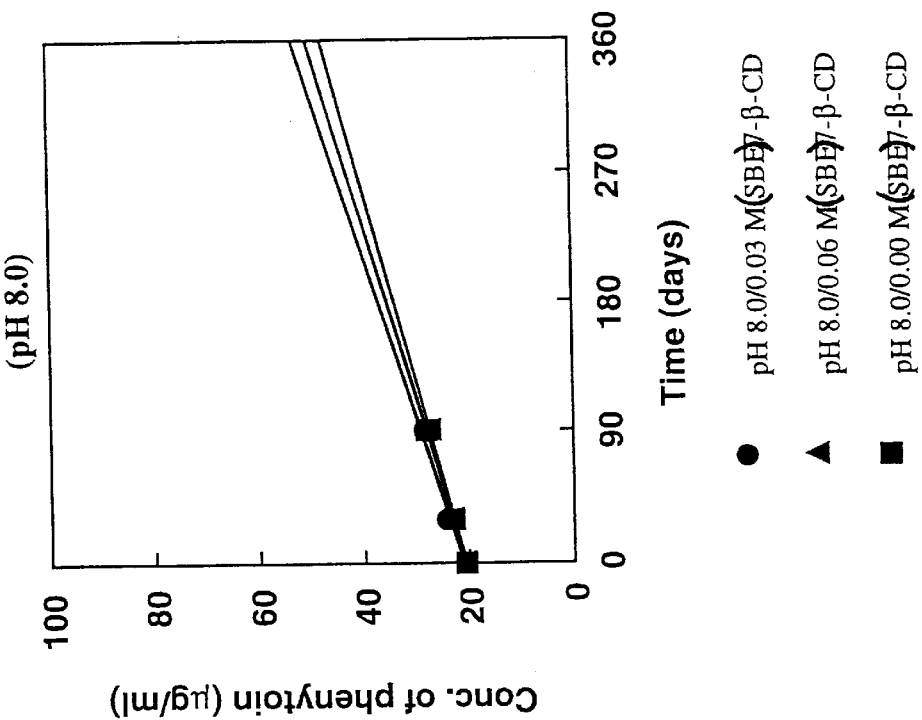
FIG. 2C shows the effects of cyclodextrin (SBE)7m-β-CD on the production of phenytoin from the degradation of fosphenytoin at 25° C. and with pH 7.4/0.06M (SBE)7m-β-CD (—●—) and pH 7.4/0.00M (SBE)7m-β-CD (—▲—).
Figure 2D:
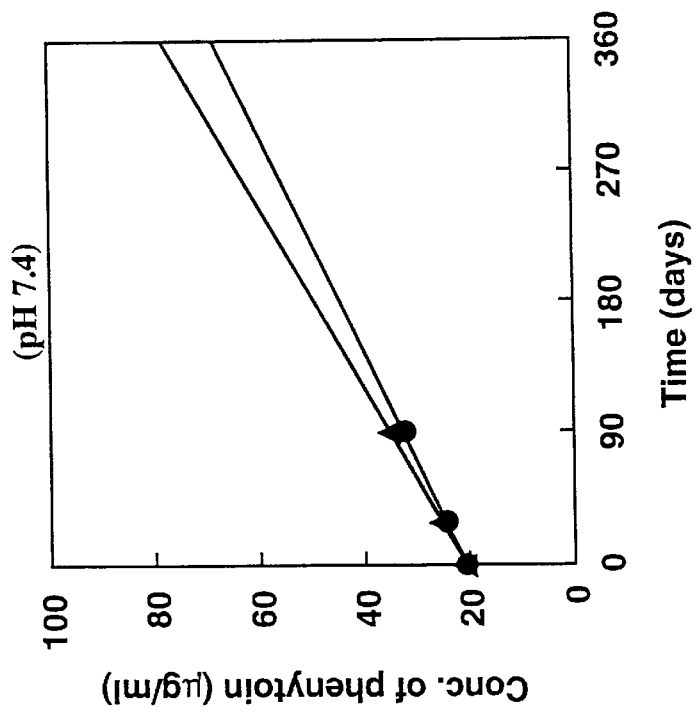
FIG. 2D shows the effects of cyclodextrin (SBE) 7m-β-CD on the production of phenytoin from the degradation of fosphenytoin at 25° C. and with pH 8.0/0.03M (SBE)7m-β-CD (—●—); pH 8.0/0.06M (SBE)7m-β-CD (—▲—); and pH 8.0/0.00M (SBE)7m-β-CD (—■—).

One object of the present invention is to provide pharmaceutical compositions of polar drugs or prodrugs having an extended shelf-life comprising cyclodextrin, a pharmaceutically active agent or prodrug and a pharmaceutically acceptable carrier, wherein the cyclodextrin is present as less than 75%, most preferably 50%, equimolar amounts of the active agent.

Many polar drugs and prodrugs have a limited shelf-life not due to a loss in potency in the compounds themselves but due to the nucleation/precipitation of their degradants which are poorly water soluble. The presence of particulate species is undesirable, particularly with injectable drugs and prodrugs. Because of the poor solubility of the degradants of many drugs and prodrugs, degradation of as little as 0.1% will often result in an unusable drug composition. Because of the propensity to degradation and poor solubility of degradation products, an adequate shelf-life, at least 2 years, is difficult or impossible to obtain for many drugs and prodrugs, particularly at neutral pH values and when stored without refrigeration.

The present invention is drawn to compositions which comprise small amounts of cyclodextrins, less than 50% equimolar amounts, in addition to the drug or prodrug and a pharmaceutically acceptable carrier. The cyclodextrin prevents the formation of particulate matter and precipitate in the pharmaceutical composition by solubilizing the degradation products as they form.

Polar drugs or prodrugs encompassed by the present invention are those drugs which tend to bind poorly to cyclodextrins because of their polarity but decompose to degradants that tend to have a higher binding affinity for the cyclodextrins thus allowing for solubilization of the degradant in the presence of the polar drug or prodrug.

Of further interest for the present invention are drugs and prodrugs which themselves may be soluble in an aqueous solution but which have degradants which are neutral and therefore sparingly soluble.

Those drugs and prodrugs which themselves are charged but whose degradants are neutral are particularly suitable for the present compositions. Negatively charged drugs or prodrugs are particularly well suited because they will not bind as strongly to the also negatively charged cyclodextrin, like the sulfoalkyl ethers described in U.S. Pat. No. 5,134,127, thus allowing very small amounts of cyclodextrin to be used.

Drugs and prodrugs which are suitable for the present compositions include steroid phosphates, hemisuccinates of steroids, and chloramphenicol, and estrogen sulfates. Examples of drugs to be used in the present compositions include, but are not limited to, hydrocortisone, dexamethasone, methylprednisolone, prednisolone, prednisolone acetate, $O^6$-benzyl guanine, and chloramphenicol. The present invention further encompasses compositions comprising prodrugs of any of the aforementioned drug compounds.

Of particular interest is the prodrug fosphenytoin, which may be present as either fosphenytoin dihydrate or anhydrous fosphenytoin and which degrades into the non-polar drug phenytoin at pH values <8.5.

Cyclodextrins (CD) are a group of cyclic homologous oligosaccharides that are obtained from the degradation of starch by the action of the enzyme cyclodextrin transglycosylase elaborated by the bacterium *Bacillus macerans*. Published methods exist for the production of cyclodextrin transglycosylase as well as making and isolating the cyclodextrins.

Cyclodextrins are cyclic molecules containing six or more α-D-glycopyranose units linked at the 1,4 positions by α linkages as in amylose. As a consequence of this cyclic arrangement, the molecule is characterized as having neither a reducing end group nor a non-reducing end group.

The molecule is represented below by schematic formula (1) where the hydroxyl groups are shown in the 2, 3, and 6-positions of the glucopyranose units.

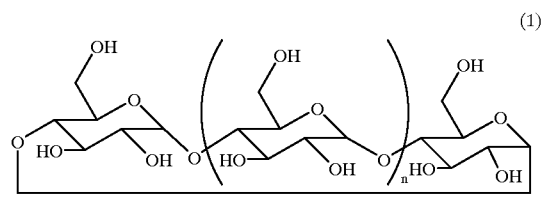

(1)

Variable n may be a number from 4 to 6, or higher.

When n=4 the molecule is commonly known as the α-cyclodextrin or cyclohexamylose, when n=5 the molecule is commonly known as β-cyclodextrin or cycloheptaamylose and when n=6 the molecule is commonly known as γ-cyclodextrin or cyclooctaamylose. When reference is made here to "cyclodextrin," it is intended to include the foregoing forms of cyclodextrin as well as molecules where n>6.

Preferred cyclodextrins are those described in U.S. Pat. No. 5,134,127 and have a structure represented by the following formula (2):

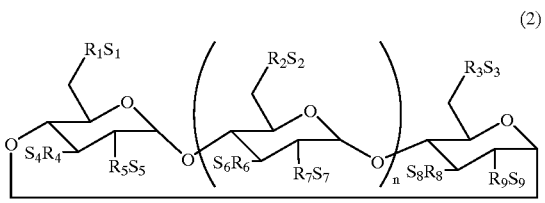

(2)

wherein:

n is 4, 5 or 6;

$R_1$, $R_2$, $R_3$, $R_4$, $R_5$, $R_6$, $R_7$, $R_8$ and $R_9$ are each, independently, $O^-$ or a $O\text{-}C_{2\text{-}6}$-alkylene)-$SO_3^-$ group, wherein at least one of $R_1$ and $R_2$ is independently a $O\text{-}(C_{2\text{-}6}\text{-alkylene})\text{-}SO_3^-$ group, preferably a $O\text{-}(CH_2)_m SO_3^-$ group, wherein m is 2 to 6, preferably 2 to 4, (e.g. $OCH_2CH_2CH_2SO_3^-$ or $OCH_2CH_2CH_2CH_2SO_3^-$); and $S_1$, $S_2$, $S_3$, $S_4$, $S_5$, $S_6$, $S_7$, $S_8$, and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amines cations such as the cations $C_{1\text{-}6}$ alkylamines, piperidine, pyrazine, $C_{1\text{-}6}$ alkanolamine and $C_{4\text{-}8}$ cycloalkanolamine.

In another preferred embodiment (2):

$R_1$ is a $O\text{-}(C_{2\text{-}6}\text{-alkylene})\text{-}SO_3^-$ group, preferably a $O\text{-}(CH_2)_m SO_3^-$ group (e.g. $OCH_2CH_2CH_2SO_3^-$ or $OCH_2CH_2CH_2CH_2SO_3^-$);

$R_2$ to $R_9$ are $O^-$;

$S_1$ to $S_9$ are as defined in embodiment (1), supra.

In another preferred embodiment (3):

$R_1$, $R_2$ and $R_3$ are each, independently, a $O\text{-}(C_{2\text{-}6}\text{-alkylene})\text{-}SO_3^-$ group, preferably a $O\text{-}(CH_2)_m SO_3^-$ group, (e.g. $OCH_2CH_2CH_2SO_3^-$ or $OCH_2CH_2CH_2CH_2SO_3^-$);

$R_4$ to $R_9$ are $O^-$; and $S_1$ to $S_9$ are as defined in embodiment (1), supra.

In another preferred embodiment (4):

$R_1$ to $R_3$ are as defined in embodiments (2) or (3), supra;
at least one of $R_4$, $R_6$ and $R_8$ is a O-($C_{2-6}$-alkylene)-$SO_3^-$ group, preferably a O-$(CH_2)_m SO_3^-$ group (e.g., $OCH_2CH_2CH_2SO_3^-$ or $OCH_2CH_2CH_2CH_2SO_3^-$);

$R_5$, $R_7$ and $R_9$ are O$^-$; and $S_1$ to $S_9$ are as defined in embodiment (1), supra.

In another preferred embodiment (5s):

$R_1$, $R_2$, $R_3$, $R_4$, $R_6$ and $R_8$ are each, independently, a O-($C_{2-6}$-alkylene)-$SO_3^-$ group, preferably a O-$(CH_2)_m SO_3^-$ group (e.g. $OCH_2CH_2CH_2SO_3^-$ or $OCH_2CH_2CH_2SO_3^-$)

$R_5$, $R_7$ and $R_9$ are O$^-$; and $S_1$ to $S_9$ are as defined in embodiment (1) supra.

Most preferred among the cyclodextrins are those wherein the $C_{2-6}$ alkylene is a $C_3$ or $C_4$ alkylene.

As a result of the two separate polar regions and the changes in solvent structure that occur upon complexation, cyclodextrins have the ability to form complexes with a variety of organic and inorganic molecules.

It is contemplated that any cyclodextrin may be used for the present compositions which has been selected as being suitably non-toxic. Suitable non-toxic cyclodextrins may be selected in accordance with the teachings of the prior art, for example, from U.S. Pat. No. 5,134,127; Loftsson and Brewster, J. Pharm. Sci. 85:1017–1025 (1996); and Okimoto et al., Pharm. Rsch. 13:256–264 (1996).

Of particular interest are the sulfobutyl ether (SBE) cyclodextrins and hydroxypropyl (HP) cyclodextrins. Cyclodextrins are added to the present compositions in general, less than 75%, most preferably less than 50%, equimolar amounts as the drug or prodrug. Although, for some specific cases, high cyclodextrin concentrations might be necessary. Preferably, the cyclodextrin is added in <50% equimolar amounts, more preferably less than 25% equimolar amounts to the drug or prodrug. More specifically, the amount of cyclodextrin would be that quantity that is capable of solubilizing the poorly soluble degradant in the presence of larger quantities of the parent drug or prodrug. The amount/concentration needed can be estimated by performing phase solubility analysis studies. The first aspect being to determine the effect of increasing cyclodextrin concentration on the solubility of the degradant at the pH values in question and the second aspect being the effect of increasing cyclodextrin concentration on the solubility of the degradant in the presence of the expected formulation of the parent drug or prodrug. This would allow one to determine the optimal concentration of cyclodextrin needed to solubilize the expected amount of degradant formed over the hoped for shelf-life of the product.

Suitable pharmaceutical carriers for the present invention include any aqueous carriers which are useful for administering the drug or prodrug, preferably those which are non-toxic, otherwise inert, medically acceptable and compatible with both the drug/prodrug and cyclodextrin. Particularly useful are buffer/saline based carriers. The present compositions may further comprise other active ingredients such as antimicrobial agents and other enabling agents such as preservatives.

The present compositions are typically prepared for injectable formulations. But may also be suitable for liquid oral products, ophthalamic products etc. The pharmaceutically active agent or prodrug will typically be present in a concentration of 1–250 mg/ml, more preferably 1–100 mg/ml. The present compositions are further formulated as close to physiologically acceptable pH values as possible. In the case of fosphenytoin the pH of the present compositions is between 7.0–8.5, preferably between 7.4–8.5, more preferably between 7.4–8.0.

It is further contemplated that the present invention encompasses freeze-dried/lyophilized compositions containing the drug or prodrug and an amount of cyclodextrin sufficient to solubilize poorly soluble degradants when the dried composition is reconstituted. That is, the cyclodextrin is typically present in the freeze-dried composition in less than 75% equimolar equivalents with the prodrug or drug, preferably less than 50% equimolar amounts, more preferably less than 25% equimolar amounts.

The present freeze-dried formulations may be prepared using conventional methods such as preparing a solution of prodrug/drug and cyclodextrin in a suitable pharmaceutical carrier and at a desired pH and the thusly prepared solution is then lyophilyzed/freeze-dried such that the freeze-dried composition need only be reconstituted with water, or other acceptable vehicles, to provide the desired pharmaceutical composition.

The present invention is further drawn to a method of extending the shelf-life of drugs and prodrugs which have insoluble degradation products by adding small amounts of cyclodextrin to the formulation. With the present method, the cyclodextrin is added at generally less than 75% equimolar amounts, preferably less than 50% equimolar amounts, more preferably less than 25% equimolar amounts.

The cyclodextrin may be added as either concentrated liquid forms of the cyclodextrin or as solid cyclodextrins such that the final solution contains the required final concentration of cyclodextrin to achieve the desired effect.

EXAMPLES OF THE INVENTION

Of particular interest in the present invention are compositions of the charged soluble prodrug forms of very insoluble drugs. One example of a soluble prodrug of an aqueous insoluble drug is fosphenytoin. Fosphenytoin is the prodrug form of phenytoin.

At pH values greater than 1.0 and less than 8.0, fosphenytoin degrades predominantly into the active drug form phenytoin. However, because the solubility of phenytoin at pH values <8 is very poor, 20–25 µg/ml, drug formulations of fosphenytoin are made at pH values >8.0. However the higher pH values make fosphenytoin more unstable and above pH 8.0 fosphenytoin further degrades into hydantoic acid derivatives, as well as 5,5-diphenylglycinamide and 5,5-diphenyl-4-imidazolidinone which are more water soluble than phenytoin. The following scheme (1) shows the degradation pattern of fosphenytoin at 1<pH<8 or at pH>8.

Scheme 1
DEGRADATION OF FOSPHENYTOIN

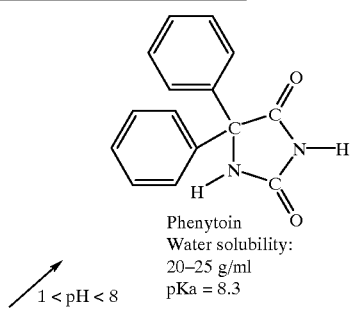

Phenytoin
Water solubility:
20–25 g/ml
pKa = 8.3

1 < pH < 8

-continued

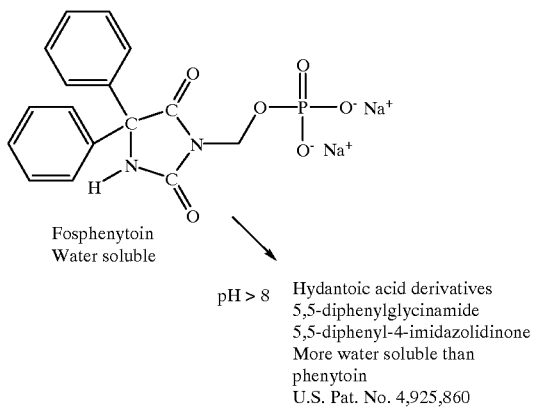

Fosphenytoin
Water soluble pH > 8    Hydantoic acid derivatives
         5,5-diphenylglycinamide
         5,5-diphenyl-4-imidazolidinone
         More water soluble than
         phenytoin
         U.S. Pat. No. 4,925,860

Although some amount of fosphenytoin degradation can be reduced with refrigeration of the pharmaceutical composition, it is desirable to have a fosphenytoin composition which has a neutral pH>7.0 and <8.0, and which can be stored without refrigeration for at least two years. By adding small amounts, less than 75%, most preferably less than 50%, equimolar amounts, of cyclodextrin to the formulation, a pharmaceutical composition of fosphenytoin is accomplished which has a neutral pH and which may be stably stored without refrigeration for at least two years.

It has been known in the prior art, as discussed above, to solubilize drugs by use of cyclodextrins. For that purpose, prior art compositions contained cyclodextrins in greater than or at least equimolar amounts compared to the drug to be solubilized. But in the present invention, much lower than equimolar amounts of cyclodextrin are utilized. Since one of the preferred cyclodextrins is negatively charged, it minimally complexes with the negatively charged fosphenytoin compared to phenytoin (Table I). Instead, as fosphenytoin degrades (at 1<pH<8) to the neutral phenytoin, the phenytoin becomes complexed to the cyclodextrin, remaining water soluble instead of precipitating out of solution. Since the function of the cyclodextrin is to bind the relatively small amount of degradation product, the cyclodextrin can be utilized in relatively small amounts, essentially in an amount necessary to complex with the amount of expected phenytoin degradation product over the desired shelf life of the pharmaceutical composition comprised of fosphenytoin.

(1) Production of phenytoin from the degradation of fosphenytoin

The chemical stability of fosphenytoin was investigated in 0.02M tris buffer solutions at pH values of 7.4 and 8.0. Fosphenytoin concentration (as its dihydrate) was 80.6 mg/ml. This is equivalent to 75 mg/ml anhydrous fosphenytoin and on a mole basis, this is also equivalent to 50 mg/ml sodium phenytoin. The solutions were filtered through a 0.2 $\mu$m membrane filter (Disposal Sterile Syringe Filter, cellulose acetate membrane, 25 mm, Corning Glass Works, N.Y.) before filling into 1 ml glass ampules (Pre-scored funnel top ampule, Fisher Scientific, Pittsburgh, Pa.) to remove fine particulate matter and for sterility purposes. The ampules were stored in an oven at 60° C. and periodically removed and analyzed for phenytoin content. The concentration of phenytoin in ampules versus time was quantitated to determine the initial rates of phenytoin production. In all cases, phenytoin production followed apparent zero-order kinetics with linear correlation coefficients of >0.99. Another earlier eluting peak was also quantitated and compared to phenytoin production. At pH 8.0, this peak had an area comparable to that of phenytoin while at pH 7.4 phenytoin was the major degradant peak observed. The results of these studies are presented in FIG. 1 as the average of duplicate runs.

(2) Production of phenytoin from the degradation of fosphenytoin in the presence of cyclodextrin The production of phenytoin from the degradation of fosphenytoin in the presence of cyclodextrin was investigated as described in (1) above with the following changes that at pH 7.4 the reactions were run in the presence of 0 and 60 mM (SBE)7m-$\beta$-CD and at pH 8.0 reactions were run in the presence of 0, 30, and 60 mM (SBE) 7m-$\beta$-CD.

These reactions were additionally carried out at 25° C., in a temperature-controlled water bath, or ovens at 37° C. or 50° C., with sampling times adjusted according to expected reactivities at differing temperatures. The results of these experiments are presented in FIGS. 2A–2D, as the average of duplicate runs.

(3) Binding constants ($M^{-1}$) for phenytoin/(SBE)7m-$\beta$-CD and fosphenytoin/(SBE)7m-$\beta$-CD An excess amount of phenytoin was added to 1 ml of tris buffer solutions in the presence (80.6 mg/ml) or absence of fosphenytoin dihydrate as a function of various amounts of (SBE) 7m-$\beta$-CD (0–80 mM). After sonication and mixing by vortex mixer, the phenytoin-suspended solutions were placed in a shaking, temperature controlled water bath for at least 5 days at 25° C. After equilibration, checked by periodic sampling, the suspensions were filtered through a membrane filter (Acrodisc, PVDF 0.2 $\mu$m, Gelman). The filtrate was isolated and diluted with HPLC mobile phase and the concentration of phenytoin was determined by HPLC. This work was performed in duplicate.

In order to predict time for phenytoin precipitation from fosphenytoin degradation, phenytoin solubility was measured in the absence and presence of fosphenytoin at 25° C. The fosphenytoin concentration of 80.6 mg/ml (75 mg/ml anhydrous fosphenytoin) was the same as the commercial product. The solubility of phenytoin was 18.1 $\mu$m/ml in the absence of fosphenytoin and 49.8 $\mu$m/ml in the presence of fosphenytoin at a pH 7.4. At a pH 8.0, the solubility of phenytoin was 27.5 $\mu$m/ml in the absence of phenytoin and 61.9 $\mu$m/ml in the presence of fosphenytoin. The slightly higher solubilities at pH 8.0 relate well to the pKa value of 8.06–8.33 for phenytoin (AHFS Drug Information; McEvoy, G. K. Eds. Amer. Soc. of Hospl. Pharmacists, 1279–1283, 1993). The solubility of phenytoin is elevated in the presence of fosphenytoin probably through micellar or complex formation (Anderson et al. J. Pharm. Sci. 74 375–381; Muller et al. Int. J. Pharm. 75 201–209, 1991).

Figure 3:
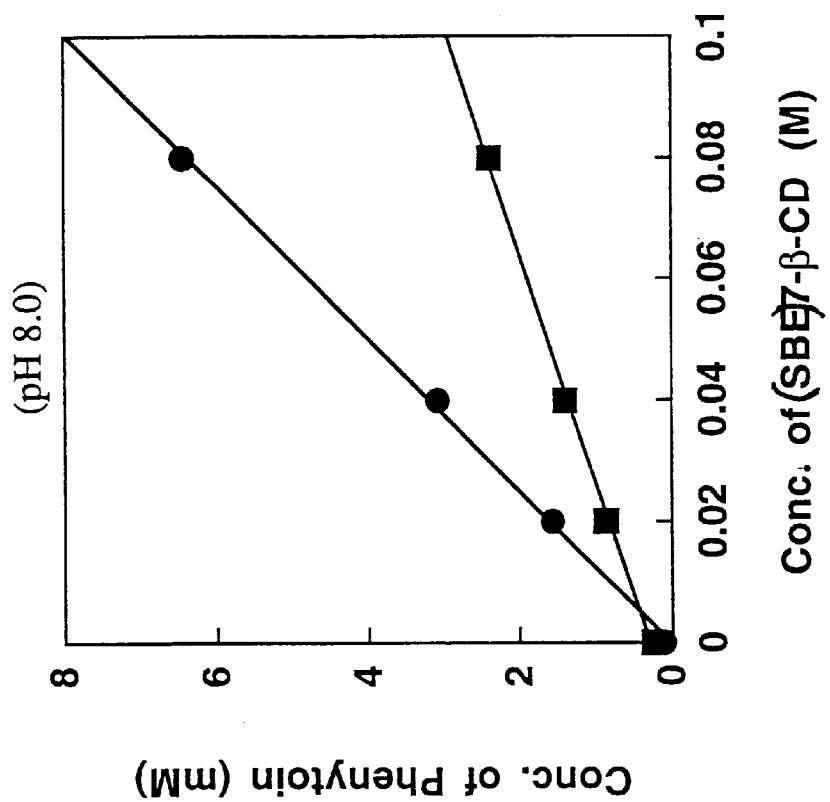
FIG. 3 shows a phase solubility diagram for phenytoin/(SBE)7m-β-CD system at pH 7.4 and pH 8.0 in the absence (●) or presence (■) of fosphenytoin. The concentration of fosphenytoin is 80.6 mg/ml.
Figure 3:
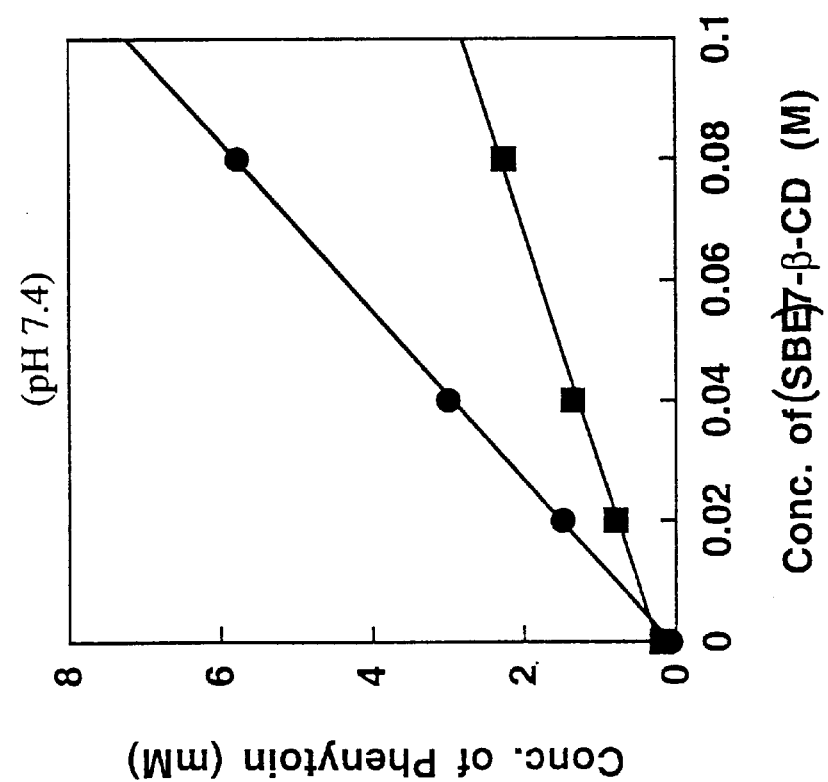

Phenytoin has been found to interact with $\beta$-CD (Tsuruka et al. Yakugaku Zasshi 101 360–367, 1981). FIG. 3 shows the phase solubility diagrams for phenytoin with (SBE)7M-$\beta$-CD at 25° C. in the presence or absence of 80.6 mg/ml of fosphenytoin in 0.02 M tris buffer solution at pH values 7.4 (FIG. 3a) and 8.0 (FIG. 3b), respectively. All phase solubility diagrams are AL-type, according to the classification of Higuchi et al. (Higuchi, T. and Connors K. A. Adv. Anal. Chem. Instrum. 4 117–212, (1965)), suggesting 1:1 phenytoin/(SBE)7m-$\beta$-CD complex formation at both pH values. Since fosphenytoin can compete with phenytoin for (SBE)7m-$\beta$-CD binding, the solubility enhancement in the presence of fosphenytoin, as expected, was lower than that in the absence of fosphenytoin.

This phenomena is illustrated in Scheme (2). The binding constant for the phenytoin/(SBE)7m-$\beta$-CD complex, $K_1$ can be calculated by the slope and intercept of the data from FIG. 3 (absence of fosphenytoin) according to Eq 2 (Hiquchi, T and Connors K. A.)

$$K_1 = \text{Slope/Intercept}(1-\text{Slope}) \tag{2}$$

$K_2$, the binding constant for the fosphenytoin/(SBE)7m-β-CD complex can be calculated according to Eq. 6 as follows;

$$K_1 = (St-So')/(St-(St-So'))(Lt-(St-so')-x)$$

$$K_1 = \text{Slope}/So'(1-\text{Slope}-x/Lt) \tag{3}$$

$$K_2 = x/(St'-x)(Lt-(St-So')-x$$

$$= (x/Lt)/(St'-x)(1-\text{Slope}-x/Lt) \tag{4}$$

From Eq. 3, $$x/Lt = 1-\text{Slope}-\text{Slope}/K_1So' \tag{5}$$

Eq. 4 and Eq. 5 lead to Eqs. 6 and 7, $$K_2 = (1/(St'-x))K_1So'/\text{Slope}-So'K_1-1) \tag{6}$$

$$\approx (1/St')(K_1So'/\text{Slope}-So'K_1-1) \tag{7}$$

where various terms are defined in Scheme (2). The term, St'-x, in Eq. 6 represents the free fraction of fosphenytoin in the presence of CD and theoretically should change with increasing CD concentration. However, since the binding of fosphenytoin to the CD is weak and on a molar basis, CD concentration was always less than St', Eq. 6 can be approximated to Eq. 7 allowing an estimation of $K_2$. This assumption seems reasonable since the phase solubility diagrams for the Scheme (2)
Competitive Inclusion of Phenytoin and
Fosphenytoin with (SBE)$_{7m}$-β-CD

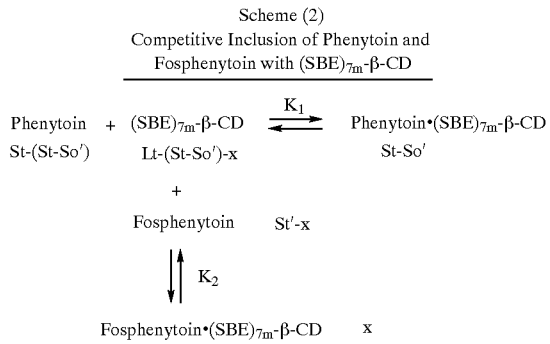

St: Total phenytoin concentration in the presence of fosphenytoin
So': Phenytoin solubility in the presence of fosphenytoin
St': Total fosphenytoin concentration
Lt: Total (SBE)$_{7m}$-β-CD concentration
x: Concentration of fosphenytoin-(SBE)$_{7m}$-β-CD complex
$K_1$: Binding constant of phenytoin and (SBE)$_{7m}$-β-CD complex
$K_2$: Binding constant of fosphentoin and (SBE)$_{7m}$-β-CD complex phenytoin/(SBE) 7m-β-CD system in the presence of fosphenytoin as shown in FIG. 3 was linear in the range of (SBE)7m-β-CD concentration investigated.

The values of $K_1$ and $K_2$ at pH values 7.4 and 8.0 are listed in Table I. The $K_1$ value at pH 8.0 was found to be smaller than pH 7.4. A reasonable explanation for this observation is that a reasonable fraction of phenytoin at pH 8.0 is in its anionic form (AHFS Drug Information, McEvoy, G. K. (eds) Amer. Soc. of Hospt. Pharmacists 1279–1283, 1993) and anionically charged drugs interact weakly with (SBE)7m-β-CD (Okimoto et al, Pharm. Res. 13 256–254, 1996), $K_2$ was found to be much smaller than $K_1$ at both pH levels, consistent with the dianionic nature of fosphenytoin at both pH values. Earlier work from this laboratory (Okimoto et al.) showed weaker interaction of anionically charged drugs with (SBE)7m-β-CD presumably due to coulombic repulsion.

TABLE I

Binding Constants ($M^{-1}$) for Phenytoin - (SBE)$_{7m}$-β-CD Complex and Fosphenytoin - (SBE)$_{7M}$-β-CD Complex at 25° C.

| System | pH 7.4 | pH 8.0 |
|---|---|---|
| Phenytoin - (SBE)$_{7M}$-β-CD ($K_1$) | 1073 | 792 |
| Fosphenytoin - (SBE)$_{7M}$-βCD ($K_2$) | 39 | 34 |

(4) Effects of cyclodextrin of shelf-life of fosphenytoin

Based on the solubility analysis, and initial projection of phenytoin production from a preliminary study at 60° C. (results included in Table II) in the absence of (SBE)7M-β-CD, 60 mM (SBE)7m-β-CD was chosen as the desired CD concentration at pH 7.4 while 30 mM and 60 mM concentrations were chosen for pH 8.0.

Figure 4:
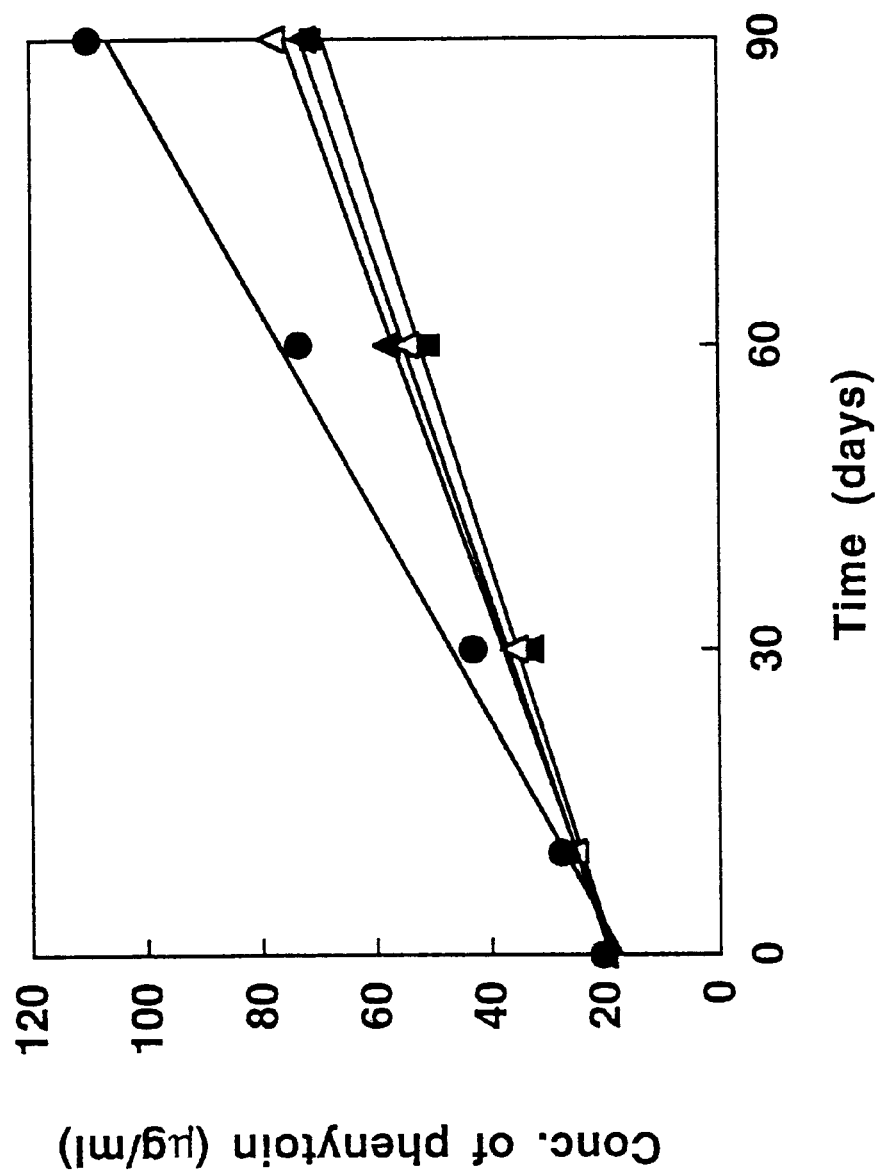
FIG. 4 shows the production of phenytoin from degradation of fosphenytoin at 37° C. in 0.02M tris buffer solution. Key: (●), pH 7.4/60 mM (SBE)7m-β-CD; (Δ), pH 8.0/ without (SBE)7m-β-CD; (▲), pH 8.0/30 mM (SBE)7M-β-CD; (■), pH 8.0/60 mM (SBE)7m-β-CD.

FIG. 4 shows typical plots of initial phenytoin production profiles versus time at 37° C. At all temperature conditions investigated, phenytoin production followed similar pseudo zero-order kinetics; phenytoin is produced linearly at all temperatures, CD concentrations and at both pH values. Since the concentration of fosphenytoin (80.6 mg/ml as its dihydrate, 180 mM) is higher than that of (SBE)7m-β-CD (30 or 60 mM) and because the binding of fosphenytoin to (SBE)7m-β-CD is very weak (see Table I), (SBE)7m-β-CD did not appear to influence the phenytoin production rate although here was a very slight trend to greater stability with increasing (SBE)7m-β-CD concentration. Initial phenytoin production rates are summarized in Table II.

Figure 5:
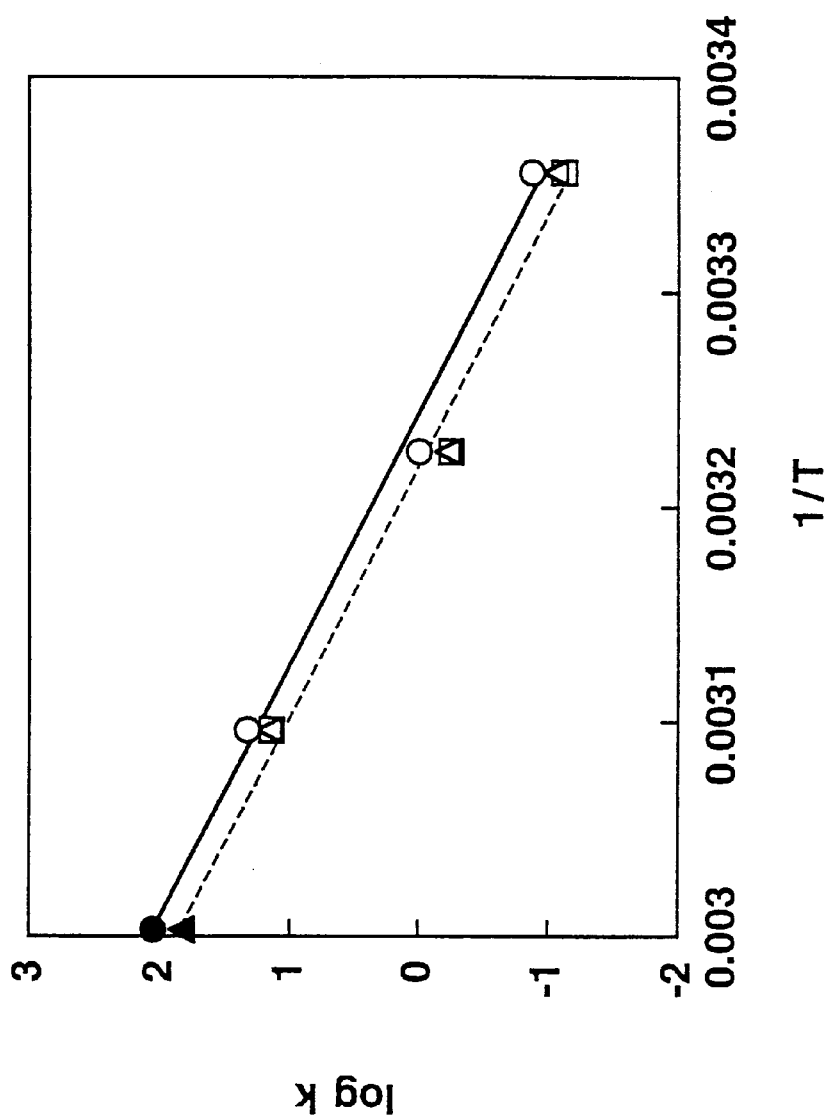
FIG. 5 presents an arrhenius plot for phenytoin production rates from fosphenytoin degradation. Key: (o), pH 7.4/60 mM (SBE)7m-β-CD; (Δ), pH 8.0/30 mM (SBE)7m-β-CD; (□), pH 8.0/60 mM (SBE)7m-β-CD; (●), pH 7.4/without (SBE)7m-β-CD;(▲), pH 8.0/without (SBE) 7m-β-CD; —, regression line for pH 7.4; - - - , regression line for pH 8.0.

FIG. 5 shows Arrhenius plots for phenytoin production rate from fosphenytoin. The apparent energy activating, Ea, values were found to be 38.9 kcal/mol for pH 7.4 and 39.5 kcal/mol for pH 8.0. These values are higher than those reported previously; 30.8 kcal/mol and also are higher than Ea values reported from most other drug degradation studies (10–30 kcal/mol) (Yoshioka, S. Stability of Drugs and Dosage Forms, Nankodo Co. Ltd., Tokyo, 1995; pp.30–67). One possible explanation for the difference may be the effect of temperature on the pH of tris buffer solutions. It was found that the pH of the tris buffer solution used here dropped to pH 6.77 at 50° C., even though the pH was adjusted at 7.40 at 25° C. Consequently, the change of phenytoin production rate can attribute not only to the direct effect of temperature on the kinetics but also the effect of temperature on pH. Since our principal goal was to study the effect of temperature on the stability of some protype formulations, buffer pH values were not adjusted at each temperature.

Table 3 lists projected shelf-lives at 25° C. which can be calculated from the rate data in Table 2. Two different shelf-life criteria were considered; time to exceed phenytoin solubility in the presence and absence of (SBE)7m-β-CD and 0.5% phenytoin production. Since 80.6 mg/ml of fosphenytoin dihydrate is equivalent to 50 mg/mL of sodium phenytoin or 46 mg/ml of phenytoin, 0.5% phenytoin production corresponds to 230 μm/ml phenytoin. When 60 mM (SBE)7m-β-CD was used, phenytoin should not precipitate for over two years at 25° C. at either pH value; the most stable formulation, which is a combination of pH 8.0 and 60 mM of (SBE)7m-β-CD concentration, suggested that phenytoin precipitation should not occur for at least 17 years if maintained at 25° C. Using the 0.5% phenytoin production as the cut-off criteria, greater than two year shelf-lives are also possible. Obviously, the amount of (SBE) 7m-β-CD could be adjusted to meet other phenytoin production criteria. These results clearly indicate that physically stable formulations of greater than two years at 25° C. of fosphenytoin in the pH range 7.4–8.0 should be possible.

Table IV presents exemplified formulae for fosphenytoin formulations having a shelf-life of either two or three years.

Each of the patents/publications noted herein is hereby incorporated in its entirety.

TABLE II

Rate of Phenytoin Production at Various Temperatures

| | Temperature | Rate (μg/mL/day) | | |
|---|---|---|---|---|
| pH | (° C.) | 0 mM CD | 30 mM CD | 60 mM CD |
| 7.4 | 25 | 0.160 | — | 0.133 |
| 7.4 | 37 | — | — | 0.993 |
| 7.4 | 50 | — | — | 21.37 |
| 7.4 | 60 | 111.8 | — | — |
| 8.0 | 25 | 0.083 | 0.088 | 0.075 |
| 8.0 | 37 | 0.634 | 0.600 | 0.562 |
| 8.0 | 50 | — | 14.43 | 13.82 |
| 8.0 | 60 | 67.20 | — | — |

TABLE III

Shelf-Life of Fosphenytoin at 25° C. Based on Phenytoin Production Rates and Solubility

| | | Solubility Criteria | | Stability Criteria | |
|---|---|---|---|---|---|
| pH | (SBE)$_{7m}$-β-CD Conc. (mM) | Phenytoin Conc. (μg/mL) | Shelf-Life[a] (Year) | Phenytoin Conc. (μg/mL) | Shelf-Life[b] (Year) |
| 7.4 | 0 | 49.8 | 0.9 | — | — |
| 7.4 | 60 | 450.8 | 9.3 | 230.0 | 4.7 |
| 8.0 | 0 | 61.9 | 2.0 | — | — |
| 8.0 | 30 | 274.4 | 8.5 | 230.0 | 7.2 |
| 8.0 | 60 | 475.5 | 17.4 | 230.0 | 8.4 |

[a]Time to exceed phenytoin solubility.
[b]Time to exceed amount of phenytoin equivalent to 0.5% degradation; 80.6 mg/mL of fosphenytoin (dihydrate) is equivalent to 46.0 mg/mL of phenytoin or 50.0 mg/mL of sodium phenytoin. Therefore, 0.5% degradation produces 230 mg/ml of phenytoin.

TABLE IV

Formulae of Two Years or Three Years Shelf-Life at 25° C.

| | Fosphenytoin | Conc. of (SBE$_{7m}$-β-CD (nM) | | Degradation (% of phenytoin) | |
|---|---|---|---|---|---|
| pH | (mg/mL) | 2 years | 3 years | 2 years | 3 years |
| 7.4 | 80.6 | 8.0 | 17.0 | 0.25 | 0.38 |
| 8.0 | 80.6 | 0.0 | 3.0 | 0.13 | 0.20 |

What is claimed is:

1. A pharmaceutical composition comprising cyclodextrin, fosphenytoin and a pharmaceutically acceptable carrier, wherein the cyclodextrin is present at less than 75% equimolar amounts of the fosphenytoin.

2. The pharmaceutical composition of claim 1, wherein the pharmaceutically acceptable carrier is aqueous.

3. The pharmaceutical composition of claim 1, wherein the cyclodextrin is present at less than 50% equimolar amounts of the fosphenytoin.

4. The pharmaceutical composition of claim 1, wherein the cyclodextrin is present at less than 25% equimolar amounts of the fosphenytoin.

5. The pharmaceutical composition of claim 1, wherein the cyclodextrin is selected from the group consisting of sulfo alkyl ether cyclodextrins and hydroxypropyl-β-cyclodextrins.

6. The pharmaceutical composition of claim 1, wherein the pH of said composition is 7.0–8.5.

7. The pharmaceutical composition of claim 1, wherein the pH of said composition is 7.0–8.0.

8. A method of extending the shelf-life of a pharmaceutical composition of fosphenytoin which comprises combining said fosphenytoin at least one cyclodextrin at less than 75% total equimolar amount of said fosphenytoin.

9. A method of extending the shelf-life of a pharmaceutical composition of fosphenytoin which comprises combining said fosphenytoin in that at least one cyclodextrin at less than 75% equimolar amount to said fosphenytoin to form a solution; and freeze drying or lyophilizing said solution.

10. A pharmaceutical composition comprising cyclodextrin and a water-soluble pharmaceutically active agent or prodrug wherein the cyclodextrin is present at less than 75% equimolar amounts of the active agent or prodrug.

11. The dried pharmaceutical composition of claim 10 which further comprises an additional pharmaceutically acceptable carrier.

12. The pharmaceutical composition of claim 10 wherein the cyclodextrin is present at less than 50% equimolar amounts of the active agent or prodrug.

13. A method of extending the shelf-life of a water-soluble pharmaceutically active agent or prodrug which comprises combining at least one cyclodextrin at less than 75% total equimolar amount of said pharmaceutically active agent or prodrug to a composition containing a pharmaceutically active agent or prodrug to increase the solubility of a poorly water soluble degradant of said pharmaceutically active agent or prodrug.

14. A method of extending the shelf-life of a water-soluble pharmaceutically active agent or prodrug comprising;

adding one or more cyclodextrins at less than 75% equimolar amount to said pharmaceutically active agent or prodrug to said pharmaceutically active agent or prodrug and a pharmaceutically acceptable carrier thereof to form a solution; and freeze drying or lyophilizing said solution to increase the solubility of a poorly water-soluble degradant of said pharmaceutically active agent or prodrug.

15. A pharmaceutical composition comprising an injectable polar drug or prodrug which produces an insoluble degradant, cyclodextrin and a pharmaceutically acceptable carrier wherein said cyclodextrin is present as less than 75% equimolar amounts of said polar drug or prodrug.

16. The pharmaceutical composition of claim 15, wherein said pharmaceutically acceptable carrier is aqueous.

17. The pharmaceutical composition of claim 15, wherein said cyclodextrin is present as less than 50% equimolar amounts of said polar drug or prodrug.

18. The pharmaceutical composition of claim 15, wherein said cyclodextrin is present as less than 25% equimolar amounts of said polar drug or prodrug.

19. The pharmaceutical composition of claim 15, wherein said cyclodextrin is selected from the group consisting of sulfo alkyl ether cyclodextrins and hydroxypropyl-β-cyclodextrins.

20. The pharmaceutical composition of claim 15, wherein said injectable polar drug or prodrug is selected from the group consisting of steroid phosphates, hemisuccinates of steroids and chloramphenicol, and estrogen sulfates.

21. The pharmaceutical composition of claim 15, wherein said polar prodrug is fosphenytoin.

22. The pharmaceutical composition of claim 21, wherein the pH of said composition is 7.0–8.5.

23. A freeze dried pharmaceutical composition which is administered by injection after being dissolved in liquid comprising a polar drug or prodrug which produces an insoluble degradant and cyclodextrin.

24. The freeze-dried pharmaceutical composition of claim 23, further comprising a freeze-dried pharmaceutically acceptable carrier.

25. The freeze-dried pharmaceutical composition of claim 23, wherein said cyclodextrin is present at less than 50% equimolar amounts of said active polar drug or prodrug.

26. A method of extending the shelf-life of a pharmaceutical composition, said pharmaceutical composition comprising an injectable polar drug or prodrug which produces an insoluble degradant, comprising adding one or more cyclodextrins to said injectable polar drug or prodrug.

27. A method of extending the shelf-life of a pharmaceutical composition, said pharmaceutical composition comprising an injectable polar drug or prodrug which produces an insoluble degradant, comprising adding one or more cyclodextrins to said injectable polar drug or prodrug and freeze drying or lyophilizing said solution.

* * * * *